(12) United States Patent
Karbing et al.

(10) Patent No.: US 10,390,711 B2
(45) Date of Patent: Aug. 27, 2019

(54) AUTOMATIC LUNG PARAMETER ESTIMATOR FOR MEASURING OXYGEN AND CARBON DIOXIDE GAS EXCHANGE

(75) Inventors: Dan Stieper Karbing, Aalborg (DK); Steen Andreassen, Aalborg (DK); Claus Lindholt, Brønderslev (DK); Stephen Edward Rees, Aaborg (DK)

(73) Assignee: Mermaid Care A/S, Nørresundby (DK)

( * ) Notice: Subject to any disclaimer, the term of this patent is extended or adjusted under 35 U.S.C. 154(b) by 1007 days.

(21) Appl. No.: 13/989,339

(22) PCT Filed: Nov. 26, 2010

(86) PCT No.: PCT/DK2010/050326
§ 371 (c)(1),
(2), (4) Date: Sep. 10, 2013

(87) PCT Pub. No.: WO2012/069051
PCT Pub. Date: May 31, 2012

(65) Prior Publication Data
US 2013/0345572 A1    Dec. 26, 2013

(51) Int. Cl.
*A61B 5/083*    (2006.01)
*A61B 5/0205*    (2006.01)
(Continued)

(52) U.S. Cl.
CPC .......... *A61B 5/0205* (2013.01); *A61B 5/083* (2013.01); *A61B 5/14542* (2013.01);
(Continued)

(58) Field of Classification Search
CPC ....... A61B 5/082; A61B 5/0097; A61B 5/083; A61B 5/14542; A61B 2016/1025;
(Continued)

(56) References Cited

U.S. PATENT DOCUMENTS

| | | | |
|---|---|---|---|
| 7,008,380 B1* | 3/2006 | Rees | A61B 5/08 128/204.23 |
| 2008/0194980 A1* | 8/2008 | Gisolf | A61B 5/029 600/526 |

FOREIGN PATENT DOCUMENTS

| | | |
|---|---|---|
| EP | 0 753 320 A1 | 1/1997 |
| EP | 2 098 163 A1 | 9/2009 |

(Continued)

OTHER PUBLICATIONS

International Search Report for PCT/DK2010/050326 dated Aug. 2, 2011.
(Continued)

*Primary Examiner* — Puya Agahi
(74) *Attorney, Agent, or Firm* — Dinsmore & Shohl LLP

(57) ABSTRACT

The invention relates to a device for determining two or more respiratory parameters relating to an individual and a method for determining two or more respiratory parameters relating to an individual by means of the device. The disclosed device and method may be used in an individual suffering from pulmonary gas exchange problems relating to gas exchange of oxygen and/or carbon dioxide, e.g. a patient with chronic obstructive pulmonary disease. The device and method may also be used in a healthy individual or in an animal, e.g. for research experiments. The device has detection means for oxygen and carbon dioxide contents in inspired and expired gas and blood. The device is controlled by a computer with functionality for entering oxygenation, carbon dioxide and acid-base values from one or more blood samples from arterial, venous, central venous or mixed venous blood samples, and with the parameter estimation based on equations of gas exchange of both oxygen and carbon dioxide and equations describing the acid-base
(Continued)

chemistry of blood potentially including the competitive binding of oxygen and carbon dioxide to hemoglobin.

33 Claims, 4 Drawing Sheets

(51) Int. Cl.
  *A61B 5/145* (2006.01)
  *A61M 16/12* (2006.01)
  *A61B 5/00* (2006.01)
  *A61B 5/08* (2006.01)
  *A61B 5/029* (2006.01)
  *A61M 16/10* (2006.01)

(52) U.S. Cl.
  CPC ........... *A61B 5/7278* (2013.01); *A61M 16/12* (2013.01); *A61B 5/0097* (2013.01); *A61B 5/029* (2013.01); *A61B 5/082* (2013.01); *A61M 2016/103* (2013.01); *A61M 2016/1025* (2013.01); *A61M 2202/0208* (2013.01); *A61M 2230/432* (2013.01); *A61M 2230/435* (2013.01)

(58) Field of Classification Search
  CPC .... A61B 2016/103; A61M 2016/1025; A61M 2016/103
  See application file for complete search history.

(56) References Cited

FOREIGN PATENT DOCUMENTS

WO    WO 00/13581       3/2000
WO    WO 2007/062531 A1  6/2007

OTHER PUBLICATIONS

Karbing, Dan S. et al., "Minimal model quantification of pulmonary gas exchange in intensive care patients" Medical Engineering & Physics, Nov. 2, 2010, pp. 240-248, vol. 33.

Karbing, Dan Stieper "Physiological models of gas exchange in decision support of mechanical ventilation—Prospective evaluation in an intensive care unit" Center for Model-based Medical Decision Support Department of Health Science and Technology Aalborg University, Nov. 27, 2009.

Loeppky, Jack A. et al., "Validation of a two-compartment model of ventilation/perfusion distribution" Respiratory Physiology & Neurobiology, 2006, pp. 74-92, vol. 151.

* cited by examiner

AUTOMATIC LUNG PARAMETER ESTIMATOR FOR MEASURING OXYGEN AND CARBON DIOXIDE GAS EXCHANGE

CROSS REFERENCE TO RELATED APPLICATIONS

This application is a U.S. National Phase Application of PCT International Application Number PCT/DK2010/050326, filed on Nov. 26, 2010, designating the United States of America and published in the English language. The disclosures of the above-referenced applications are hereby expressly incorporated by reference in their entireties.

FIELD OF THE INVENTION

The present invention relates to a device for determining at least two respiratory parameters relating to an individual. The invention also relates to a corresponding method, a corresponding computer system, and a corresponding computer program product.

BACKGROUND OF THE INVENTION

The lungs function both to secure the transport of oxygen ($O_2$) from inspired gas to the blood for metabolism by the cells, and that the byproduct of metabolism, carbon dioxide ($CO_2$), is transported from the blood to the alveolar air to be expired. The function of the lungs in this process, known as pulmonary gas exchange, is vital for maintaining homeostatis, and pulmonary gas exchange disorders as seen for example in patients with chronic obstructive pulmonary disease (COPD), postoperative patients and the critically ill are major causes of death in hospitalized patients, and are associated with large socioeconomic costs in and out of hospitals.

In individuals where pulmonary gas exchange is compromised, blood levels of $O_2$ and $CO_2$ are affected differently by the underlying causes of gas exchange problems. The most common cause of pulmonary gas exchange problems is ventilation/perfusion ($\dot{V}/\dot{Q}$) mismatch, where pulmonary shunt ($\dot{V}/\dot{Q}=0$) and alveolar dead space ($\dot{V}/\dot{Q}=$infinite) represent the extremes. The transport of $O_2$ from the lungs to the blood is most affected by pulmonary shunt and regions of the lung with low $\dot{V}/\dot{Q}$ ratios caused by pulmonary injuries such as atelectasis and airway closure. In contrast, the transport of $CO_2$ from the blood to the lungs is most affected by alveolar dead space and regions of the lung with high $\dot{V}/\dot{Q}$ ratios.

Whilst $O_2$ and $CO_2$ are affected differently by pulmonary gas exchange disorders, transport of the two gases in the body is not independent. Both $O_2$ and $CO_2$ are transported in the body by blood with the mechanisms for binding the two gases in blood being different. $O_2$ is mainly transported bound to haemoglobin, whereas $CO_2$ is mainly transported in the form of bicarbonate ($HCO_3$). The transport of $O_2$ and $CO_2$ is coupled through effects known as the Bohr-Haldane effects and correct description of transport of both these gasses requires consideration of these effects.

In clinical practice, pulmonary gas exchange problems are normally evaluated using surrogate measures which give a poor indication of the true underlying problems. $O_2$ gas exchange problems are normally evaluated using pulse oximetry oxygen saturation measurements or oxygen partial pressure or saturation analysed from an arterial blood sample. Whilst these measures indeed may indicate whether there is a $O_2$ gas exchange problem in the form of hypoxemia, they vary with changes in therapy not affecting the gas exchange status of the patient, such as changes in inspired oxygen fraction ($FiO_2$), and they do not allow a discrimination between whether the underlying cause is low $\dot{V}/\dot{Q}$ or shunt, for which treatment can differ.

A previous patent describes the Automatic Lung Parameter Estimator (hereinafter referred to as the ALPE patent, or the ALPE device/system); U.S. Pat. No. 7,008,380 B, which is hereby incorporated by reference in its entirety. The patent describes a device for evaluating pulmonary gas exchange with reference to the transport of oxygen. This device has been shown to describe pulmonary gas exchange of oxygen accurately in several patient groups successfully separating the cause of $O_2$ gas exchange problems into that arising due to shunt and low $\dot{V}/\dot{Q}$.

For $CO_2$, measurements in clinical practice include an arterial blood sample giving the partial pressure of $CO_2$ and the pH showing whether $CO_2$ level is abnormal and whether it has led to an acidosis/alkalosis. In addition alveolar deadspace can be estimated from capnography but this is not normally performed outside the operating theater.

Despite early physiological modeling efforts in the 1940's forming much of our current understanding of pulmonary gas exchange, $O_2$ and $CO_2$ have traditionally been measured and evaluated independently. However, there is a clear improvement potential in combining $O_2$ and $CO_2$ in measurements and analysis acquiring a synergistic effect allowing relevant interactions between $O_2$ and $CO_2$ to be described and exploiting all available information resulting in more accurate and physiological description of pulmonary gas exchange.

Hence, an improved device for evaluating pulmonary gas exchange would be advantageous, and in particular a more efficient and/or reliable device would be advantageous.

SUMMARY OF THE INVENTION

It is a further object of the present invention to provide an alternative to the prior art.

In particular, it may be seen as an object of the present invention to provide a device that solves the above mentioned problems of the prior art with quantifying oxygen and carbon dioxide pulmonary gas exchange in an individual resulting in two or more respiratory parameters.

Human patients with gas exchange problems are of particular interest, e.g. patients with hypoxemia or lung disease, but the device may also be used in healthy human subjects, farm animals, domestic animals, and pet animals used for experiments.

Thus, the above described object and several other objects are intended to be obtained in a first aspect of the invention by providing a device for determining at least two respiratory parameters relating to an individual, comprising a gas flow device having means for conducting a flow of inspiratory gas from an inlet opening to the respiratory system of the individual and a flow of expiratory gas from the respiratory system of the individual to an outlet opening, a gas-mixing unit for supplying a substantially homogeneous gas to the inlet opening of the gas flow device, first supply means for supplying a first gas to an inlet of the gas mixing unit and having first control means for controlling the flow of the first gas, second supply means for supplying a second gas having an oxygen fraction different to the gas supplied from the first supply means to an inlet of the gas mixing unit and having second control means for controlling the flow of the second gas, a computer for determining said two or more respiratory parameters, first detection means for detecting the level of oxygen in the blood circulation of the individual and producing an output to the computer accordingly, and second detection means for detecting the level of oxygen in the gas flow passing into or out of the respiratory system of the individual and producing an output to the computer, first carbon dioxide detection means for detecting the level of carbon dioxide in the blood circulation of the individual and producing an output to the computer accordingly, and second carbon dioxide detection means for detecting the level of carbon dioxide in the gas flow passing into or out of the respiratory system of the individual and producing an output to the computer accordingly, the computer being adapted for retrieving and storing at least two oxygen measurements and one carbon dioxide measurement, the oxygen measurements being the concurrent output produced by the first detection means and the second detection means within a data structure, in which the two stored outputs are mutually related and related to a stored oxygen measurement at a corresponding level of oxygen in the gas flow passing into the respiratory system, the carbon dioxide measurement being the concurrent output produced by the first carbon dioxide detection means and the second carbon dioxide detection means within a data structure, in which the two stored outputs are mutually related and related to a stored carbon dioxide measurement at a corresponding level of oxygen in the gas flow passing into the respiratory system, the computer further being adapted for determining at least two respiratory parameters being descriptive of the pulmonary gas exchange of oxygen and/or carbon dioxide of the individual, the determination being based on the at least two oxygen measurements and one carbon dioxide measurement.

In short, the present invention may provide a device for estimating parameters indicative of gas exchange of both $O_2$ and $CO_2$, in particular in patients with severe lung injuries such as those presenting in the intensive care unit with acute lung injury or in patients with COPD, both patient groups where improvement in understanding and more appropriate therapy could lead to significant reductions in mortality and socioeconomic costs.

It should be noted that previously quantitative analysis of pulmonary gas exchange was possible, but clinicians to some extent relied on oversimplified methods when evaluating pulmonary gas exchange in patients with respiratory failure. Thus, almost 60 years ago the work by Rahn and Riley and Cournand made quantitative analysis of pulmonary gas exchange possible but some assumptions underlying their work may be rendered obsolete by the present invention.

In clinical practice single measurements or model parameters are usually used to describe the effects of abnormalities in pulmonary gas exchange of $O_2$ and $CO_2$. In describing $O_2$ exchange, these include pulse oximetry, venous and arterial blood gas measurements, intrapulmonary shunt, or the oxygen partial pressure in arterial blood to inspired oxygen fraction ratio ($PaO_2/FiO_2$). These values have in common that they vary with extrapulmonary factors such as ventilation and variation in inspired oxygen fraction ($FiO_2$). In describing $CO_2$ exchange clinical parameters include venous and arterial blood gas measurements, expired $CO_2$ levels, and calculation of physiological or alveolar dead space. When describing pulmonary gas exchange all single parameter models of both $O_2$ and $CO_2$ have the problem that they lump intrapulmonary effects into one pathophysiological description.

The present invention is advantageous in that appropriate modeling using the detected level of $CO_2$ in the blood, the invention is facilitating patient specific interpretation of pulmonary gas exchange of $O_2$ and $CO_2$ at a degree much closer to the true physiological picture than current available clinical measurements, perhaps representing the optimal compromise between complexity and feasibility as required for a so-called 'minimal' model useful in clinical applications.

The present invention may further be seen as an advantageous modification of the ALPE device for measurement of $CO_2$ in inspired and expired gas as well as blood. In addition, an embodiment of the invention may also include software for analyzing the measurements provided by the device incorporating equations describing the acid-base chemistry of blood as well as $O_2$ and $CO_2$ gas exchange. FIG. 1 illustrates an example of the measurement data included for describing pulmonary gas exchange of $O_2$ and $CO_2$, in the illustrated case a patient with severe lung injury. Also illustrated is the fit of a pulmonary gas exchange model to measurement data. In comparison to the original ALPE device a new subplot has been added with $CO_2$ measurement data and model fit. Further details on FIG. 1 will be provided below.

In the context of the present invention, an oxygen measurement or a carbon dioxide measurement may be constituted by two corresponding measured inputs, e.g. a point in a coordinate system or a graph like FIG. 1, as it will be appreciated by the skilled reader considering the frame work of the mentioned oxygen measurement or the mentioned carbon dioxide measurement.

Advantageously, the first detection means for detecting the level of oxygen may detect parameters in the blood circulation of the individual, such as $SaO_2$, $SpO_2$, $CaO_2$, $PaO_2$, or $PpO_2$, or any combination thereof, or equivalents or derived parameters thereof.

Advantageously, the second detection means for detecting the level of oxygen may detect parameters in the gas flow passing into or out of the respiratory system of the individual, such as $FiO_2$, $FE'O_2$, $FEO_2$, $PiO_2$, $PE'O_2$, or $PEO_2$, or any combination thereof, or equivalents or derived parameters thereof.

Advantageously, the first carbon dioxide detection means for detecting the level of carbon dioxide may detect parameters in the blood circulation of the individual, such as $PaCO_2$, $CaO_2$ (e.g. by blood gas measurements), $PtcCO_2$ (e.g. by transcutaneous measurements), or any combination thereof, or equivalents or derived parameters thereof. The transcutaneous measurements may be performed by commercially available probes from e.g. Radiometer Medical, Sentec or Philips IntelliVue.

Advantageously, the second carbon dioxide detection means for detecting the level of carbon dioxide in the gas flow passing into or out of the respiratory system of the individual, such as $PiCO_2$, $FiCO_2$, $PECO_2$, $FECO_2$, $PE'CO_2$, or $FE'CO_2$, or any combination thereof, or equivalents or derived parameters thereof.

Advantageously, the computer may be adapted for determining at least two respiratory parameters such as Rdiff, shunt, $\dot{V}/\dot{Q}$, $\dot{V}$-distribution, $\dot{Q}$-distribution, H-shift, V-shift, or $CO_2$-shift, or any combination thereof, or equivalents or derived parameters thereof.

Advantageously, the said respiratory parameters may be generalized parameters being comparable to similar parameter(s) determined for other individuals e.g. to facilitate comparison with reference values and/or other individuals.

In a preferred embodiment, the computer may be adapted for determining the at least two respiratory parameters selected from
 a parameter indicative of the ventilation of the individual,
 a parameter indicative of the perfusion of the individual, and
 a parameter indicative of a ratio between a parameter indicative of the ventilation of the individual, and a parameter indicative of the perfusion of the individual.

It should be noted that, in some cases, the selection may be performed so that the at least two parameters may be indicative of the ventilation of the individual, i.e. within the same group. In particular, the computer may comprise a lung model, the model comprising two ventilated compartments and a pulmonary shunt compartment.

In an embodiment, the computer may be adapted for determining two respiratory parameters selected from
 a parameter indicative of the ventilation of the individual,
 a parameter indicative of the perfusion of the individual, and
 a parameter indicative of a ratio between a parameter indicative of the ventilation of the individual, and a parameter indicative of the perfusion of the individual.

It should be noted that, in some cases, the selection may be performed so that the two parameters may be indicative of the ventilation of the individual, i.e. within the same group.

More particularly, the computer may be adapted for determining the two respiratory parameters according to a fitting model comprising:
 a first variable fitting parameter, such as fs, said variable fitting parameter being indicative of the intrapulmonary shunt fraction, and
 a second variable fitting parameter, such as fA2, said variable fitting parameter being indicative of the fraction of ventilation, distributed between the said two compartments, the variables fs and fAs being defined in more detail below.

Alternatively, the computer may be adapted for determining the two respiratory parameters according to a fitting model comprising:
 a first variable fitting parameter, such as fs, said variable fitting parameter being indicative of the intrapulmonary shunt fraction, and
 a third variable fitting parameter, such as f2, said variable fitting parameter being indicative of the fraction of perfusion distributed between the said two compartments, the variables fs and f2 being defined in more detail below.

In another embodiment, the computer may be adapted for determining three respiratory parameters selected from:
 a parameter indicative of the ventilation of the individual,
 a parameter indicative of the perfusion of the individual, and
 a parameter indicative of a ratio between a parameter indicative of the ventilation of the individual, and a parameter indicative of the perfusion of the individual.

It should be noted that, in some cases, the selection may be performed so that the one or more of the three parameters may be indicative of the ventilation of the individual, i.e. within the same group. Thus, one parameter may be indicative of ventilation, and two parameters may be indicative of perfusion, one of the two being for example the shunt.

More particularly, the computer may be adapted for determining the three respiratory parameters according to a fitting model comprising:
 a first variable fitting parameter, such as fs, said variable fitting parameter being indicative of the intrapulmonary shunt fraction,
 a second variable fitting parameter, such as fA2, said variable fitting parameter being indicative of the fraction of ventilation distributed between the said two compartments, and
 a third variable fitting parameter, such as f2, said third variable fitting parameter being indicative of the perfusion distribution fraction between the two ventilated compartments of the lung model, the variables fs, fA2 and 2s being defined in more detail below.

More specifically, the third variable fitting parameter may further be indicative of the ventilation and the perfusion to the two ventilated compartments of the lung model, In an embodiment, wherein the computer may be further adapted for performing a procedure at least once, the procedure comprises determining, based on at least two oxygen measurements and one carbon dioxide measurement, and a consistency measure indicative of the quality of the fitting model, whether additional measurements are required. Advantageously, the quality may be indicated or represented by p-value, std. deviation, reliability, accuracy, goodness of fit, residuals, or variation, etc. or any combination, and/or derivate thereof, in order to improve the fitting process.

More advantageously, the computer may be further adapted, if the consistency measure is below a predetermined threshold, to indicate type and/or magnitude of additional measurements to improve the consistency measure in order to guide and/or assist the operator or perform an automated process for improved fitting.

Even more advantageously, the computer may apply a measure to determine a quality of the cardiac output value. In patients with elevated metabolism and suspected poor circulation guesses or estimates (e.g. based on statistical models) may be poor predictors of cardiac output. In this case, it can be argued that there is a clinical need for measurement of cardiac output, and the disclosed device could direct clinicians to appropriate use of cardiac output measurements based on a calculated measure of consistency between measurements. Such consistency measures could also be used to identify uncertainties regarding other measurements and the device could provide advice to the user as to what measurements and/or estimates should be improved or performed. This advice could be based on statistical models, mathematical models, simple rules, etc., or any combination, and/or derivative thereof.

In an embodiment, the second carbon dioxide detection means may be arranged for detecting the level of carbon dioxide, such as $FiCO_2$, or $PiCO_2$, in the gas flow passing into the respiratory system, and the device further comprises
 third carbon dioxide detection means for detecting the level of carbon dioxide, such as $PECO_2$, $FECO_2$, $PE'CO_2$, or $FE'CO_2$, passing out of the respiratory system and producing an output to the computer accordingly, and
 fourth detection means for detecting variables, such as Vt, f, or $\dot{V}$, of the gas flow passing the respiratory system and producing an output to the computer accordingly, said output being sufficient for the computer to establish the volume flow of gas passing the respiratory system, the computer being adapted for retrieving and storing output from the third detection means and fourth detection means within the data structure relating these stored output mutually as well as with the output from the first and second oxygen detection means and first and second carbon dioxide detection means retrieved simultaneously.

More specifically, the computer may then be further adapted for establishing, based on said measurement(s), the oxygen consumption ($VO_2$) and carbon dioxide production ($VCO_2$) of the individual.

Typically, the carbon dioxide partial pressure in the blood circulation may be in the range of 1 kPa to 20 kPa.

In one embodiment, the first carbon dioxide detection means may typically be arranged for detecting a parameter relating to the carbon dioxide partial pressure in the arterial blood stream.

In another embodiment, the computer may be adapted to determine two or more parameters relating to an equilibrium state of the overall oxygen uptake or consumption and carbon dioxide elimination or production based on the output of at least one of the oxygen and one of the carbon dioxide detection means, to compare said parameter(s) with predefined threshold value(s) and to produce a control data item accordingly if said parameter(s) exceed said threshold value(s).

In a second aspect, the invention relates to a method for determining two or more respiratory parameters using a device according to the first aspect of the present invention, wherein the individual is an apparently healthy individual, alternatively, the individual may be considered to have a risk of suffering from oxygen and/or carbon dioxide pulmonary gas exchange problems, and more alternatively, the individual may be suffering from oxygen and/or carbon dioxide pulmonary gas exchange problems.

In third aspect, the invention relates to a computer system comprising at least one general purpose computer having one or more computer programs stored within data storage means associated therewith, the computer system being arranged for as well as being adapted for determining two or more respiratory parameters relating to an individual according to the first aspect.

In a fourth aspect, the invention relates to a computer program product embodied on a computer readable medium being adapted to enable a computer system according to the third aspect to determine two or more respiratory parameters of an individual.

The first, second, third and fourth aspect of the present invention may each be combined with any of the other aspects. These and other aspects of the invention will be apparent from and elucidated with reference to the embodiments described hereinafter.

A: Begin parameter estimation if Fi$O_2$<1.00 and Sp$O_2$>0.85
B: Continuous data recording from gas delivery unit, pulse oxymeter, transcutaneous carbon dioxide monitor and expiratory gas measurement devices.
C: Set oxygen level (Fi$O_2$).
D: Monitor $O_2$ and $CO_2$ equilibrium.
E: Equilibrium level.
F: Record measurement.
G: Sufficient number of measurements?
H: Estimate new Fi$O_2$.
I: Estimate Pulmonary Parameters.

Figure 4:
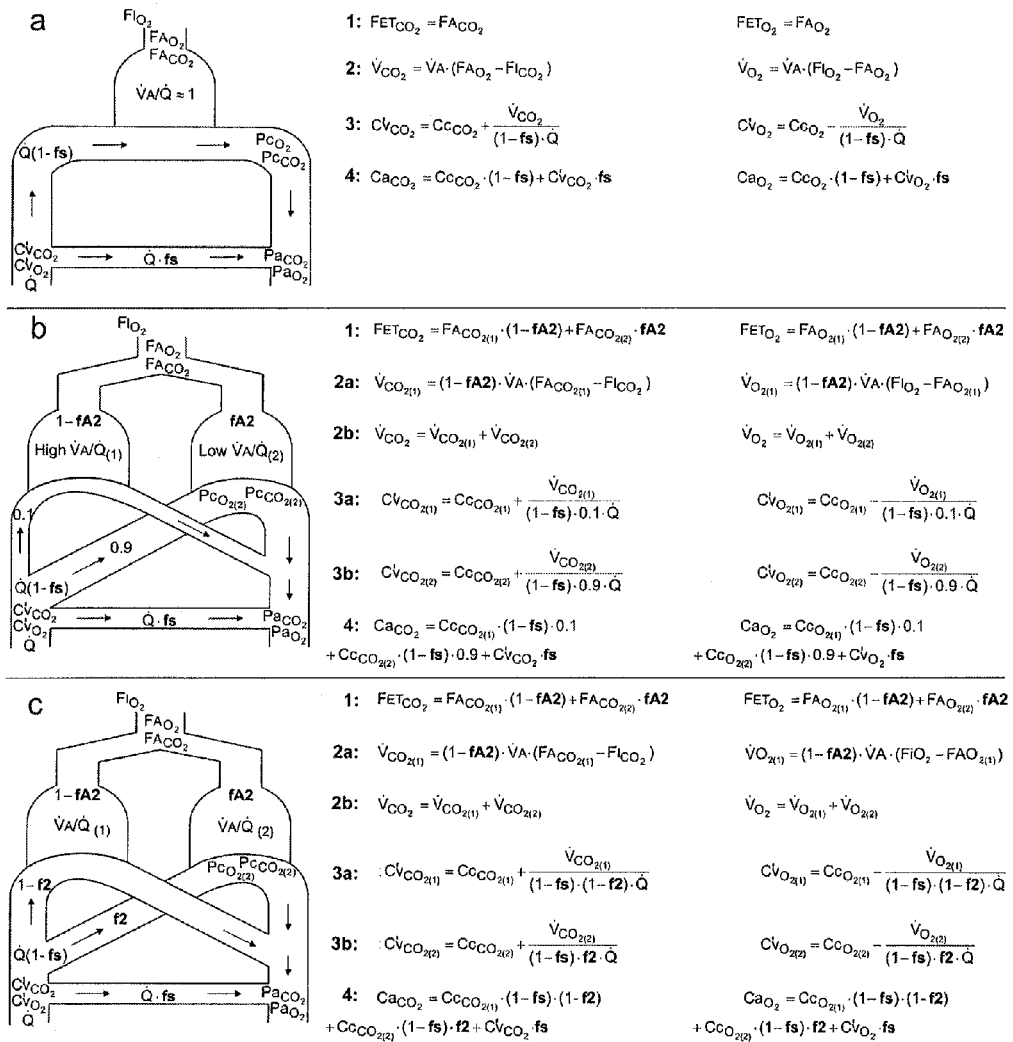

FIG. 4. Three different models of pulmonary gas exchange constituting examples of models applicable with the disclosed device (left column). Also illustrated are the individual models' specific equations for pulmonary gas exchange of $CO_2$ (middle) and $O_2$ (right). Model equations describe gas fractions (F), volume flows ($\dot{V}$), partial pressures (P) and concentrations (C) of $O_2$ and $CO_2$. Model equations describe $O_2$ and $CO_2$ in inspired gas (I), alveolar gas (A), end-tidal gas (ET), mixed venous blood ($\bar{v}$), pulmonary capillary blood (c) and arterial blood (a). Model parameters are written as bold in equations. a): One parameter model with one ventilated compartment with no $\dot{V}/\dot{Q}$ mismatch and an unventilated pulmonary shunt compartment receiving a fraction of cardiac output (fs parameter). b) Two parameter model with two ventilated compartments and a pulmonary shunt compartment (fs). The high $\dot{V}/\dot{Q}$ compartment receives 10% of non-shunted blood flow while the low $\dot{V}/\dot{Q}$ compartment receives 90%. The parameter fA2 determines ventilation distribution between the two ventilated compartments. c) Three parameter model with two ventilated compartments and a pulmonary shunt compartment (fs). Both ventilation and perfusion to ventilated compartments can be varied with the parameters fA2 and f2, respectively.

DETAILED DESCRIPTION OF THE INVENTION

One embodiment will be described. The embodiment description will focus on the modifications of the Automatic Lung Parameter Estimator (ALPE), cf. Reference 1, device for determining two or more respiratory parameters relating to an individual. The modifications of the ALPE device will allow the same fast on-line estimation of respiratory parameters completing the measurement procedure in 10-15 minutes, but also allowing calculation of respiratory parameters describing the pulmonary gas exchange of carbon dioxide in addition to oxygen. The disclosed device therefore retains the functionalities of the ALPE patent, these being:
1) On-line continuous data collection
2) Automatic assessment of the timing of measurements
3) Automatic detection of the next target $SpO_2$
4) Automatic assessment of the appropriate $FiO_2$ settings to achieve target $SpO_2$
5) Automatic control of the $FiO_2$
6) On-line parameter estimation
7) Automatic assessment of the number of measurements required To allow calculation of respiratory parameters relating to an individual describing the pulmonary gas exchange of both oxygen and carbon dioxide, it is preferable to add the following functionalities
1) Include invasive or non-invasive measurements of carbon dioxide contents of arterial blood
2) Include measurements of carbon dioxide contents in inspired and expired gases
3) Estimate or measure acid-base status of arterial blood
4) Include equations in computer software for parameter estimation describing gas exchange of oxygen and carbon dioxide and the acid-base chemistry of blood preferably including the competitive binding of oxygen and carbon dioxide to hemoglobin
5) Optionally, include carbon dioxide in assessment of the timing of measurements
6) Optionally, include carbon dioxide in assessment of the number of measurements required The resulting novel apparatus includes the ventilatory equipment, computer hardware and software as outlined below.

Figure 1:
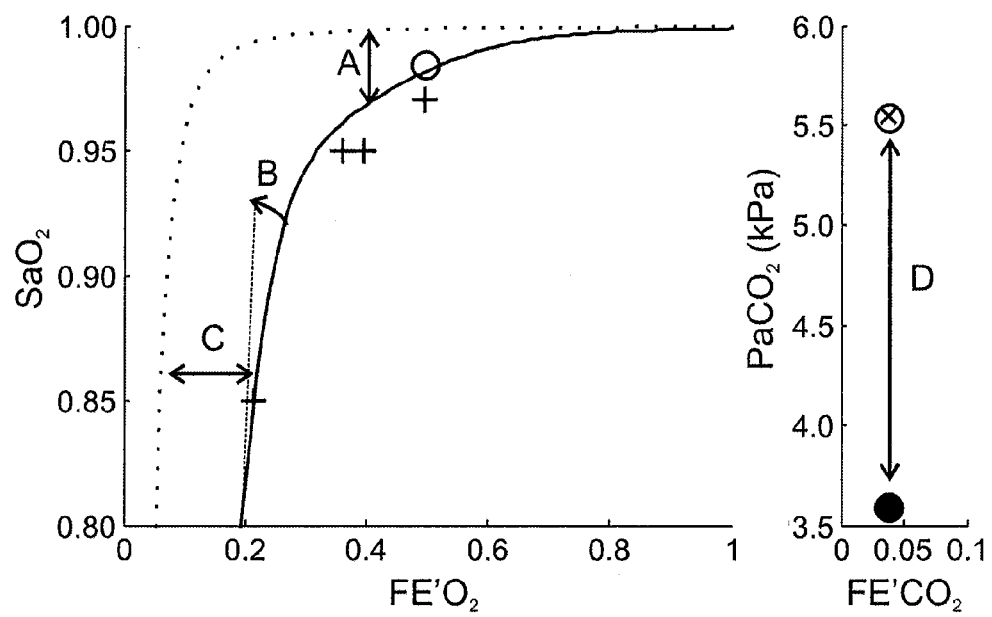
FIG. 1. The measurement data obtained with the disclosed modification of the ALPE device. Left subplot) Plot of the end-tidal oxygen fraction (FE'$O_2$, x-axis) against the arterial oxygen saturation (Measured Sa$O_2$: o, measured Sp$O_2$: +, y-axis) for a patient with severe lung injury. The solid line illustrates model fitted curve using a three parameter model (shunt, $\dot{V}$-distribution, $\dot{Q}$-distribution) [3]. Dotted line illustrates the FE'$O_2$—Sa$O_2$ curve for the patient if the patient had no gas exchange problems. Line A illustrates the vertical displacement of the curve (V-shift) due to a shunt disorder. Line B illustrates the change in slope of the vertical portion of the FE'$O_2$—Sa$O_2$ curve due to changes in perfusion between regions of the lungs with different Ventilation/Perfusion ratios. Line C illustrates the horizontal displacement of the curve (H-shift) due to a ventilation/perfusion or oxygen diffusion abnormality. Right subplot Plot of the end-tidal carbon dioxide fraction (FE'$CO_2$, x-axis) against the arterial partial pressure of carbon dioxide (Measured Pa$CO_2$: open o, y-axis) for the same severely ill patient as illustrated in the left subplot, these data constituting the added measurements obtained with the disclosed modification of the ALPE device. An x illustrates the model fitted prediction of Pa$CO_2$ using a three parameter model (shunt, $\dot{V}$-distribution, $\dot{Q}$-distribution), cf. Reference 3. The filled o illustrates the FE'$CO_2$—Pa$CO_2$ point for the patient if the patient had no gas exchange problems. Line D illustrates the displacement in carbon dioxide level ($CO_2$-shift) due to gas exchange problems.
Figure 2:
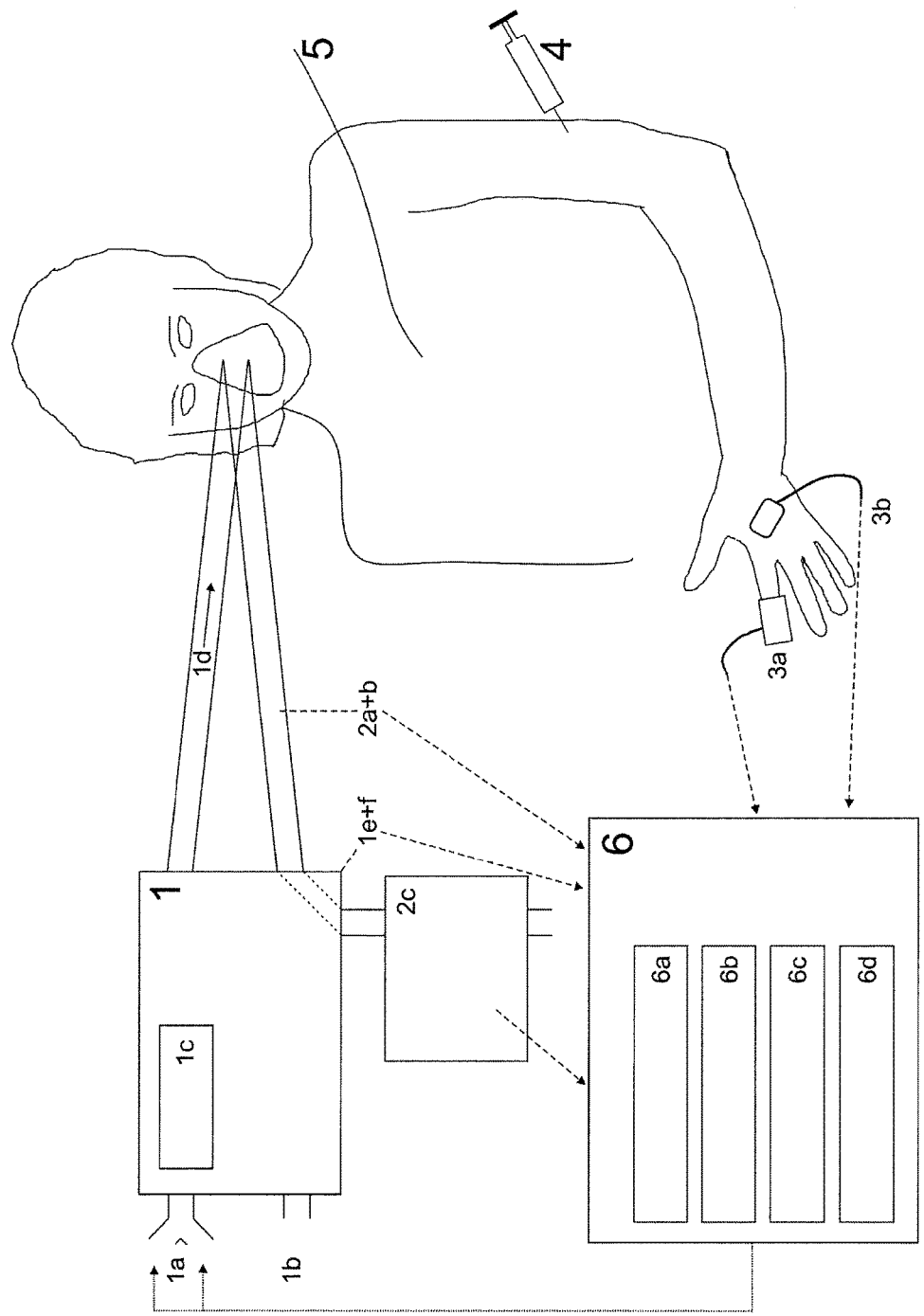
FIG. 2. An embodiment of the Automatic Lung Parameter Estimator experimental set-up working with nitrogen for sub-atmospheric oxygen levels modified with means for detecting carbon dioxide contents in gases passing into and out of the respiratory system and for continuous noninvasive measurement of arterial carbon dioxide contents. The system includes: 1) A Gas Delivery Unit including gas inlets (1a, 1b), a gas mixer (1c), a flow or pressure gradient (1d), equipment for the measurement and/or setting of inspired oxygen fraction (Fi$O_2$), tidal volume and respiratory frequency (1e) and equipment for the measurement of inspired carbon dioxide fraction (Fi$CO_2$); 2) Equipment for measurement of expired gases including an oxygen monitor placed so as to measure end tidal oxygen fraction (2a), a carbon dioxide monitor placed so as to measure end tidal carbon dioxide fraction (2b), and/or an expiratory reservoir, used with an oxygen monitor and/or a carbon dioxide monitor to measure the fraction of gas in or leaving the expiratory reservoir (FE$O_2$, FE$CO_2$) (2c); 3) Non-invasive monitoring equipment including: Measurement of arterial oxygen saturation (Sa$O_2$) via e.g. a pulse oxymeter (Sp$O_2$) (3a) and measurement of arterial carbon dioxide levels via e.g. a transcutaneous carbon dioxide monitor (Ptc$CO_2$) (3b); 4) Measurements of arterial or venous blood gas samples (optional); 5) Measurement of cardiac output (optional); 6) A computer system including software for automatic collection of data (6a), monitoring the steady state of the patients/subjects oxygenation (6b), a feedback controller for adjusting inspired oxygen fraction (6c), and estimation of gas exchange parameters (6d). Dashed arrowed lines illustrate the flow of information to the computer. Dotted arrowed lines illustrate the control of the gas delivery unit by the computer.

Description of the Automatic Lung Parameter Estimator for $O_2$ and $CO_2$ according to the present invention, in the following called ALPE2:

The ALPE2, illustrated in FIG. 2, may be used to quantify gas exchange parameters in any individual, with the parameters in patients being useful for diagnostic or monitoring purposes and in healthy subjects and animals in experiments. ALPE2 will be particularly interesting in patients with chronic or severe lung disease, e.g. patients with chronic obstructive pulmonary disease or patients with acute respiratory distress syndrome.

The ALPE2 can automatically determine the parameters of models of oxygen and carbon dioxide transport. These parameters are obtained from numerous measurements including the $FiO_2/SpO_2$ curve and at least a single measurement of the arterial carbon dioxide contents, with the combination of the carbon dioxide point and the $FiO_2/SpO_2$ curve being constructed automatically by the apparatus, the latter from $SpO_2$ varying between 0.85 to 1.00.

ALPE2 illustrated in FIG. 2 includes the following, with numbers in the text referring to the numbers in FIG. 2:
1. A gas delivery unit—This equipment being identical to the ALPE gas delivery unit, i.e. including two or more gas inlets, shown in FIG. 2 delivering a) oxygen or nitrogen, and b) air; c) a gas mixer; d) a means for delivering gases to the individual; e) equipment for measuring and/or setting inspired oxygen fraction ($FiO_2$); and f) equipment for measuring inspired carbon dioxide fraction or pressure ($FiCO_2$ or $PiCO_2$). Alternatively, $FiCO_2$ or $PiCO_2$ may be estimated, e.g. assuming that inspired carbon dioxide fraction is equal to that of room air or zero. The gas delivery unit of the ALPE2 system can either be a stand-alone device or any other device which includes the necessary functionality, e.g. a patient ventilation device.
2. Measurement of expired gases—oxygen and carbon dioxide contents of expired gases are measured using either: a) An oxygen monitor and b) a carbon dioxide monitor (i.e. a capnograph), a+b) placed to measure expired gases, and sensitive enough to allow determination of end tidal gas contents ($FE'O_2$ or $FE'O_2$, and $FE'CO_2$ or $PE'CO_2$), i.e. the oxygen and carbon dioxide contents in the gases at the end of an expiration; or c) An expiratory reservoir, placed so as to capture expiratory gases, used in combination with a carbon dioxide monitor sensitive enough to measure the carbon dioxide contents in gas in or leaving the expiratory reservoir ($FEO_2$ or $PEO_2$, and $FECO_2$ or $PECO_2$).
3. Measurement of arterial contents of oxygen and carbon dioxide—a) arterial oxygen saturation ($SaO_2$) is measured as in ALPE via e.g. a pulse oximeter ($SpO_2$); b) arterial level of carbon dioxide (i.e. partial pressure ($PaCO_2$), concentration or content) can be measured via e.g. a transcutaneous carbon dioxide monitor.
4. Measurement of arterial or venous blood samples—Measurements of arterial, peripheral venous, central venous, and mixed venous blood gas samples may be taken or monitored continuously and entered manually into the system. A single measurement of the level of $CO_2$ is necessary either through noninvasive means (see point 3 above) or through blood sampling. If via blood sample, then invasive measurements of the level of oxygenation and acid-base chemistry will also be available and can be input to the calculations performed by the device. These inputs are optional.
5. Measurement of cardiac output—Cardiac output may be measured and manually entered into the system. This measurement is optional.
6. A computer system—this system including software for:

a) Automatic collection of data from the gas delivery unit ($FiO_2$, $FiCO_2$, Vt, f), expired gas measurement devices (FE'$O_2$, FE$O_2$, FE'$CO_2$, FE$CO_2$), pulse oxymeter (or other source of $SpO_2$ or $SaO_2$), transcutaneous carbon dioxide monitor (or other optional source of monitoring $CO_2$).

b) Monitoring steady state of the individual's oxygen and carbon dioxide pulmonary gas exchange.

c) A feedback controller, which determines whether a further measurement is required considering previous oxygen and carbon dioxide measurements and automatically adjusts $FiO_2$ to the most appropriate level.

d) Estimation of respiratory parameters from the collected data describing the oxygen and carbon dioxide gas exchange status of the individual.

Dashed arrowed lines in FIG. 2 illustrate flow of information to the computer system. Dotted arrowed lines in FIG. 2 illustrate the control of the gas delivery unit by the computer.

Detailed Description of the Flowchart

The flowchart is provided solely to illustrate the invention by reference to a specific embodiment. The flowchart and the algorithms included herein, while illustrating certain aspects of the invention, do not portray the limitations or circumscribe the scope of the disclosed invention.

Figure 3:
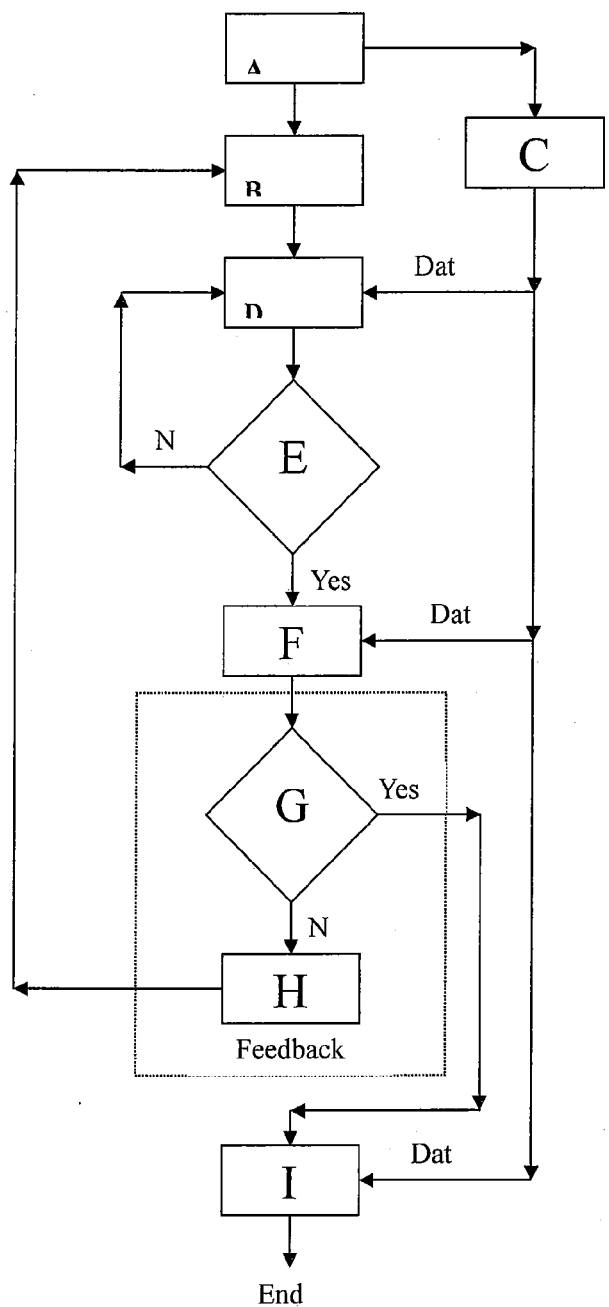
FIG. 3. Flow chart for a measurement of variables for determination of oxygen and carbon dioxide lung parameters.

FIG. 3 is a flowchart illustrating the processes involved during operation of the Automatic Lung Parameter Estimator for $O_2$ and $CO_2$ (ALPE2).

Box A: After set-up of the equipment as illustrated in FIG. 2 the parameter estimation procedure begins.

Box B: As part of this process the computer continuously collects data from the other equipment, including $FiO_2$ and $SpO_2$ (and/or FE'$O_2$, FE$O_2$, FE'$CO_2$, FE$CO_2$, Vt, f, $PtcCO_2$).

Box C: An initial inspired oxygen fraction is selected ($FiO_2$) and delivered to the patient. This is done automatically via the computer or manually by the doctor. Initially $FiO_2$ is usually that of air (21%) but any other value of $FiO_2$ can be used as the starting point for the experiment. At all times the patient/subject is required to have an arterial oxygen saturation ($SpO_2$) greater than or equal to 0.85. The initial $FiO_2$ may therefore be set to a high level so as to achieve $SpO_2 \geq 0.85$.

After setting the inspired oxygen level the patients' pulmonary gas exchange system will take time to equilibrate. This usually occurs within 2-5 minutes after the perturbation. The equilibrium of the patients pulmonary gas exchange system is monitored automatically by the "steady state monitor" software in the computer. This functionality substantially reduces the time taken to perform a parameter estimation and is only possible because of the apparatus.

Box D: The assessment of equilibrium can be performed using a number of algorithms, e.g. as follows:

1) The arterial oxygen saturation ($SpO_2$) and/or the transcutaneous carbon dioxide partical pressure ($PtcCO_2$) remain constant within a predefined range over a predefined time period.

2) The difference between the fraction of oxygen in the inspired and expired gas and/or the difference between the fraction of carbon dioxide in the inspired and expired gas remain constant within a predefined interval over a predefined time period.

3) The calculated oxygen consumption ($VO_2$) and/or the calculated carbon dioxide production ($VCO_2$) remain constant within a predefined interval for a predefined time period.

The oxygen consumption ($VO_2$) is calculated automatically by the computer from the continuously monitored variables using the equation $VO_2 = f(Vt-Vd)(FiO_2 - FE'O_2)$ assuming, measuring or calculating a value of Vd, or using $VO_2 = f\,Vt\,(FiO_2 - FEO_2)$, or any variation in this equation where a combination of measurements of end tidal or mixed expired gases are used to estimate the oxygen consumption. Similarly, the carbon dioxide production ($VCO_2$) is calculated automatically by the computer from the continuously monitored variables using the equation $VCO_2 = f(Vt-Vd)(FE'CO_2 - FiCO_2)$ assuming or calculating a value of Vd, or using $VCO_2 = f\,Vt\,(FECO_2 - FiO_2)$, or any variation in this equation where a combination of measurements of end tidal or mixed expired gases are used to estimate the carbon dioxide production.

Box E: When equilibrium is achieved a measurement is recorded (Box F).

Box F: This measurement includes the current values of all continuously monitored variables as described previously. It can also include measurements of blood gases from and arterial, peripheral venous, central venous or mixed venous blood and a cardiac output measurement obtained from equipment e.g. a pulmonary catheter. The last measurements are optional, unless arterial carbon dioxide levels are not measured continuously, in which case a single blood sample is necessary to measure blood level of carbon dioxide. Preferably the carbon dioxide level of blood is measured and related to oxygen measurements at a certain $FiO_2$ level. The measurement of carbon dioxide level of blood could, however, also in a separate aspect of the invention be performed independent of oxygen measurements, before, during or after the procedure, ignoring the measured oxygen contents in calculations limiting these from including the interactions between oxygen and carbon dioxide in describing the gas exchange of the individual.

Box G: Following a measurement it is decided either automatically by the apparatus or manually by the clinician whether a sufficient number of measurements have been performed, or whether to change the inspired oxygen fraction to a new level and take a further measurement when equilibrium is achieved.

Box H: It is also decided either automatically by the apparatus or manually by the clinician what level of $FiO_2$ should be selected for a new measurement (if necessary). An experiment consists of not less than 2 measurements at varying $FiO_2$ levels, with $SpO_2$ in the range 0.85-1.00 of which at least one measurement includes carbon dioxide level in blood, e.g. via a transcutaneous carbon dioxide monitor. It is important that the setting of $FiO_2$ levels achieve data points with $SpO_2$ well distributed between 0.85-1.00. There is no requirement of the range of carbon dioxide measurements.

Examples of algorithms, which can be used to implement Box G are included in the next section.

Box I: After an adequate set of measurements has been taken parameters are estimated which describe the individual's lung function. Parameter estimation is performed automatically using one or more of the following algorithms:

1) Graphical estimation of oxygen and carbon dioxide displacements of the $FiO_2/SpO_2$ curve (or FE'$O_2/SpO_2$ or FE$O_2/SpO_2$) and the FE'$CO_2/PtcCO_2$ point (or FE$CO_2/PtcCO_2$ or $FiCO_2/PtcCO_2$).

Values of inspired or expired oxygen fraction can be plotted against the arterial oxygen saturation ($SpO_2$) and values of inspired or expired carbon dioxide fraction can be plotted against the arterial carbon dioxide contents (e.g. $PtcCO_2$) and graphical methods used to measure the horizontal (H-shift) and vertical displacement (V-shift) of the oxygen data (or interpolated oxygen data) from a normal reference range and used to measure the displacement of carbon dioxide level ($CO_2$-shift) from a normal reference range.

2) Estimation of the parameters of models of oxygen transport.

All data collected for each of the measurements can be used with mathematical models of oxygen and carbon dioxide pulmonary gas exchange to estimate parameters describing gas exchange of oxygen and carbon dioxide. Parameters can e.g. be estimated describing the shunting of pulmonary blood (shunt) and either a resistance to gas diffusion or a mismatch between the ventilation and perfusion of the lung.

In the following, more details and results on the modeling will be provided. For further details and references, the skilled reader is referred to Reference 3, which is hereby incorporated by reference in its entirety.

The models and results presented in the following illustrate models of varying complexity (number of respiratory parameters) and a comparison of the models' ability to perform model fitted predictions of measured data from 18 intensive care patients.

Three models of increasing complexity (number of parameters) describing $O_2$ and $CO_2$ pulmonary gas exchange are described as illustrated in FIG. 4 where individual model specific equations also are listed. The models are based on continuous ventilation and perfusion, mass conservation and assume steady state. Model a is a one-parameter model, including two compartments: a shunt compartment with a parameter, fs, describing the intrapulmonary shunt fraction; and a ventilated compartment receiving all ventilation and non-shunted perfusion.

Model b is a two-parameter model, including a shunt compartment, and two ventilated compartments to describe $\dot{V}/\dot{Q}$ mismatch: a low $\dot{V}/\dot{Q}$ compartment receiving 90% of non-shunted perfusion; and a high $\dot{V}/\dot{Q}$ compartment receiving 10%. A parameter, fA2, describes the fraction of ventilation going to each ventilated compartment and thereby the degree of $\dot{V}/\dot{Q}$ mismatch.

Model c is a three-parameter model with ventilation and perfusion distributions varied between the ventilated compartments according to the fA2 and f2 parameters, respectively. Equations in FIG. 4 describe: 1) Relationship between alveolar gas contents in model compartments and end-tidal measurements; 2) $O_2$ consumption and $CO_2$ production; 3) Relationship between mixed venous gas concentrations and capillary gas concentrations in model compartments; 4) Arterial gas concentration calculated from capillary and mixed venous concentrations.

In addition to equations listed in FIG. 4, a number of equations are included for describing alveolar ventilation, capillary gas contents from alveolar or end-tidal gas contents in gas passing out of the respiratory system, etc. Also included is equations describing the acid-base chemistry of blood enabling calculation of blood $O_2$ and $CO_2$ contents (arterial, capillary and venous) taking into account interactions between $O_2$ and $CO_2$ (e.g. Bohr-Haldane effects) and the acid-base chemistry of blood.

Table 1 below shows calculated accuracy and precision of model fitted predictions of $SpO_2$, $SaO_2$, and $PaCO_2$ in 18 intensive care patients using the three models of pulmonary gas exchange illustrated in FIG. 4. Calculated precisions (normalized interquartile range of residuals (NIQR)) can be compared with the expected precisions, which are $SpO_2$: 0.02; $SaO_2$: 0.005 and $PaCO_2$: 0.09 kPa. For model c biases are small and calculated precision indicate precisions marginally better than expected levels. Biases are larger for model b compared to model c. Model b precision, however, are within expected levels. Model a can only predict $SpO_2$ with small bias and good precision, but predicts $SaO_2$ and $PaCO_2$ with poor bias and precision.

TABLE 1

Calculated accuracy (median residuals) and precision (normalized interquartile range of residuals) for model fitted predictions of SpO2, SaO2, and PaCO2 in 18 intensive care patients using the three models of pulmonary gas exchange illustrated in FIG 4.

| Prediction | Model a | | Model b | | Model c | |
| --- | --- | --- | --- | --- | --- | --- |
| | Median | NIQR | Median | NIQR | Median | NIQR |
| SpO2 | 0.004 | 0.019 | 0.013 | 0.020 | 0.006 | 0.013 |
| SaO2 | −0.012 | 0.008 | −0.004 | 0.004 | −0.003 | 0.003 |
| PaCO2 (kPa) | −1.28 | 0.66 | 0.01 | 0.01 | 0.00 | 0.00 |

Results are from Reference 3.

GLOSSARY $FiO_2$ Fraction of oxygen in inspired gas.
$PiO_2$ Pressure of oxygen in inspired gas.
$FiCO_2$ Fraction of carbon dioxide in inspired gas.
$PiCO_2$ Pressure of carbon dioxide in inspired gas.
$SaO_2$ Oxygen saturation of arterial blood, measured from a blood sample.
$CaO_2$ Oxygen concentration in arterial blood.
$PaO_2$ Pressure of oxygen in arterial blood, measured from a blood sample.
$SpO_2$ Oxygen saturation of arterial blood, measured transcutaneously.
$PpO_2$ Pressure of oxygen in arterial blood, measured transcutaneously.
$FE'O_2$ Fraction of oxygen in expired gas at the end of expiration.
$FEO_2$ Fraction of oxygen in the mixed expired gas.
$PE'O_2$ Pressure of oxygen in expired gas at the end of expiration.
$PEO_2$ Pressure of oxygen in the mixed expired gas.
$FE'CO_2$ Fraction of carbon dioxide in expired gas at the end of expiration.
$FECO_2$ Fraction of carbon dioxide in the mixed expired gas.
$PE'CO_2$ Pressure of carbon dioxide in expired gas at the end of expiration.
$PECO_2$ Pressure of oxygen in the mixed expired gas.
$PaCO_2$ Carbon dioxide partial pressure in arterial blood, measured from a blood sample.

$CaCO_2$ Carbon dioxide concentration in arterial blood.
$PtcCO_2$ Transcutaneous carbon dioxide partial pressure, measured transcutaneously.
Vt Tidal volume, i.e. volume of gas breathed per breath.
f Respiratory frequency, i.e. number of breaths per minute.
$VO_2$ Oxygen consumption, i.e. the liters of oxygen consumed by the tissues per minute.
$VCO_2$ Carbon dioxide production, i.e. the liters of carbon dioxide produced by the tissues per minute.
Vd Dead space i.e. the volume of the lung not involved in exchanging gases with the blood.
shunt Respiratory parameter representing the fraction of blood not involved in gas exchange.
Rdiff Respiratory parameter representing a resistance to oxygen diffusion across the alveolar lung capillary membrane.
$\dot{V}$ Ventilation.
$\dot{Q}$ Perfusion
$\dot{V}/\dot{Q}$ Respiratory parameter representing the balance between ventilation and perfusion of a homogeneous region of the lung.
$\dot{V}$-distribution Respiratory parameter representing fraction of ventilation going to different regions of the lungs or fraction of ventilation going to different ventilated compartments of a model of pulmonary gas exchange.
$\dot{Q}$—distribution Respiratory parameter representing fraction of perfusion going to different regions of the lungs or fraction of perfusion going to different ventilated compartments of a model of pulmonary gas exchange.
V—shift Respiratory parameter representing a vertical shift in plots of $FiO_2$ against $SaO_2$, $FiO_2$ against $SpO_2$, $FE'O_2$ against $SaO_2$, or $FE'O_2$ against $SpO_2$.
H-shift Respiratory parameter representing a horizontal shift in plots of $FiO_2$ against $SaO_2$, $FiO_2$ against $SpO_2$, $FE'O_2$ against $SaO_2$, or $FE'O_2$ against $SpO_2$.
$CO_2$-shift Respiratory parameter representing the $CO_2$-level shift in plots of $FiCO_2$ against $PaCO_2$, $FiCO_2$ against $PtcCO_2$, $FE'CO_2$ against $PaCO_2$, or $FE'CO_2$ against $PtcCO_2$.

REFERENCES

1. AUTOMATIC LUNG PARAMETER ESTIMATOR (ALPE); U.S. Pat. No. 7,008,380B1.
2. Rees S E, Kjrgaard S, Thorgaard P, Malczynski J, Toft E, Andreassen S (2002) The automatic lung parameter estimator (ALPE) system: non-invasive estimation of pulmonary gas exchange parameters in 10-15 minutes. J Clin Monit Comput 17:43-52.
3. Karbing D S, Kjrgaard S, Andreassen S, Espersen K, Rees S E. Minimal model quantification of pulmonary gas exchange in intensive care patients. Med Eng Phys. In press.
4. Rees S, Andreassen S (2005) Mathematical models of oxygen and carbon dioxide storage and transport: the acid-base chemistry of blood. Crit Rev Biomed Eng 33:209-264.
5. Andreassen S, Rees S E (2005) Mathematical models of oxygen and carbon dioxide storage and transport: interstitial fluid and tissue stores and whole body transport. Crit. Rev Biomed Eng 33:265-98.

All patent and non-patent references cited in the present application, are hereby incorporated by reference in their entirety.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

The skilled person in the field of pulmonary gas exchange would recognise that ventilation/perfusion mismatch is the primary physiological cause of gas exchange problems. However they would also recognize that a model of diffusion resistance describing impaired diffusion of oxygen and/or carbon dioxide (e.g. in different model compartments) could be applied to fit measurements of oxygen and carbon dioxide in respiratory gases and blood. In the context of the claims, the mentioning of ventilation, perfusion and/or ventilation/perfusion mismatch or ratio should not be construed as excluding parameters describing ventilation, and/or perfusion to model compartments with diffusion resistance and parameters relating to diffusion resistance or any combination thereof, or equivalents or derived parameters thereof.

Although the present invention has been described in connection with the specified embodiments, it should not be construed as being in any way limited to the presented examples. The scope of the present invention is to be interpreted in the light of the accompanying claim set. In the context of the claims, and other parts of the description, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A measuring and fitting device for fitting a gas exchange fitting model for an individual to measurement data, thereby providing a more accurate physiological description of pulmonary gas exchange for the individual, comprising:
    a computer for constructing the gas exchange fitting model comprising a set of at least three respiratory parameters relating to an individual, wherein at least two of the at least three respiratory parameters are a parameter indicative of ventilation of the individual and a parameter indicative of perfusion of the individual;
    a gas flow device having means for conducting a flow of inspiratory gas from a gas flow device inlet opening to a respiratory system of the individual and a flow of expiratory gas from the respiratory system of the individual to an outlet opening,
    a gas-mixing unit for supplying a homogeneous gas to the gas flow device inlet opening of the gas flow device,
    first supply means for supplying a first gas to a first gas mixing unit inlet of the gas mixing unit and having first control means for controlling the flow of the first gas,
    second supply means for supplying a second gas having an oxygen fraction different than the gas supplied from the first supply means to a second gas mixing unit inlet of the gas mixing unit and having second control means for controlling the flow of the second gas, first detection means for detecting a level of oxygen in a blood circulation of the individual and producing a first output to the computer accordingly, and second detection means for detecting the level of oxygen in the gas flow passing into or out of the respiratory system of the individual and producing a second output to the computer, first carbon dioxide detection means for detecting a level of carbon dioxide in the blood circulation of the individual and producing a third output to the computer accordingly, and second carbon dioxide detection means for detecting the level of carbon dioxide in the gas flow passing into or out of the respiratory system of the individual and producing a fourth output to the computer accordingly, the computer being adapted for retrieving and storing at least two oxygen measurements and one carbon dioxide measurement, the oxygen measurements being a first concurrent output comprising the first output and the second output concurrently produced by the first detection means and the second detection means within a first data structure, in which the stored first output and the stored second output are mutually related and related to a stored oxygen measurement at a corresponding level of oxygen in the gas flow passing into the respiratory system, the carbon dioxide measurement being a second concurrent output comprising the third output and the fourth output concurrently produced by the first carbon dioxide detection means and the second carbon dioxide detection means within a second data structure, in which the stored third and fourth outputs are mutually related and related to a stored carbon dioxide measurement at a corresponding level of oxygen in the gas flow passing into the respiratory system, the computer being further adapted for:

fitting the gas exchange fitting model for the individual by estimating said set of at least three respiratory parameters using the at least two oxygen measurements and one carbon dioxide measurement, taking into account that the pulmonary gas exchange of oxygen and carbon dioxide of the individual are dependent on each other, and determining, based on at least two oxygen measurements and one carbon dioxide measurement and the set of at least three respiratory parameters, a consistency measure indicative of quality of the gas exchange fitting model for the individual, the quality measure being a quality measure of the set of at least three respiratory parameters in relation to the at least two oxygen measurements and one carbon dioxide measurement, thereby determining the gas exchange fitting model for the individual, wherein the gas exchange fitting model is stored in the computer for use.

2. The measuring and fitting device according to claim 1, wherein said respiratory parameters is/are generalized parameters being comparable to similar parameter(s) determined for other individuals.

3. The measuring and fitting device according to claim 1, wherein the computer is adapted for determining at least two respiratory parameters of said at least three respiratory parameters selected from:

a parameter indicative of a ventilation of the individual,
a parameter indicative of a perfusion of the individual, or
a parameter indicative of a ratio between said parameter indicative of the ventilation of the individual, and said parameter indicative of the perfusion of the individual.

4. The measuring and fitting device according to claim 3, wherein the computer comprises a lung model, the lung model comprising two ventilated compartments and a pulmonary shunt compartment.

5. The measuring and fitting device according to claim 4, wherein the computer is adapted for determining two respiratory parameters of said at least three respiratory parameters selected from:

the parameter indicative of the ventilation of the individual,
the parameter indicative of the perfusion of the individual, or
the parameter indicative of said ratio between said parameter indicative of the ventilation of the individual, and said parameter indicative of the perfusion of the individual.

6. The measuring and fitting device according to claim 5, wherein the computer is adapted for determining the two respiratory parameters according to the fitting model comprising:

a first variable fitting parameter, said variable fitting parameter being indicative of a intrapulmonary shunt fraction, and
a second variable fitting parameter, said variable fitting parameter being indicative of a fraction of ventilation, distributed between the said two ventilated compartments.

7. The measuring and fitting device according to claim 5, wherein the computer is adapted for determining the two respiratory parameters according to the fitting model comprising:

a first variable fitting parameter, said variable fitting parameter being indicative of the intrapulmonary shunt fraction, and
a third variable fitting parameter, said variable fitting parameter being indicative of the fraction of perfusion distributed between the said two ventilated compartments.

8. The measuring and fitting device according to claim 1, wherein the computer is adapted for determining said three respiratory parameters selected from:

a parameter indicative of the ventilation of the individual,
a parameter indicative of the perfusion of the individual, or
a parameter indicative of a ratio between said parameter indicative of the ventilation of the individual, and said parameter indicative of the perfusion of the individual.

9. The measuring and fitting device according to claim 8, wherein the computer is adapted for determining the three respiratory parameters according to the fitting model comprising:

a first variable fitting parameter, said variable fitting parameter being indicative of the intrapulmonary shunt fraction,
a second variable fitting parameter, said variable fitting parameter being indicative of the fraction of ventilation distributed between two ventilated compartments of a lung model, and
a third variable fitting parameter, said third variable fitting parameter being indicative of the perfusion distribution fraction between the two ventilated compartments of the lung model.

10. The measuring and fitting device according to claim 9, wherein said third variable fitting parameter is indicative of the ventilation and the perfusion to the two ventilated compartments of the lung model.

11. The measuring and fitting device according to claim 1, wherein the computer is further adapted for performing said procedure at least once, wherein the procedure comprises:
further determining, based on said at least two oxygen measurements and one carbon dioxide measurement, and said consistency measure indicative of the quality of the fitting model, whether additional measurements are required.

12. The measuring and fitting device according to claim 11, wherein the computer is further adapted, if the consistency measure is below a predetermined threshold, to indicate type and/or magnitude of additional measurements to improve the consistency measure.

13. The measuring and fitting device according to claim 11, wherein the computer applies a measure to determine a quality of the cardiac output value.

14. The measuring and fitting device according to claim 1, wherein the second carbon dioxide detection means are arranged for detecting the level of carbon dioxide in the gas flow passing into the respiratory system, and the device further comprises:
a third carbon dioxide detection means for detecting the level of carbon dioxide passing out of the respiratory system and producing a fifth output to the computer accordingly, and fourth detection means for detecting variables of the gas flow passing the respiratory system and producing a sixth output to the computer accordingly, said fifth and sixth output being sufficient for the computer to establish the volume flow of gas passing the respiratory system, the computer being adapted for retrieving and storing fifth and sixth outputs from the third detection means and fourth detection means, respectively, within the said second data structure relating these stored outputs mutually as well as with the first and second outputs from the first and second oxygen detection means, respectively, and third and fourth outputs from the first and second carbon dioxide detection means, respectively, retrieved simultaneously.

15. The measuring and fitting device according to claim 14, wherein the computer is further adapted for establishing, based on said measurement(s), an oxygen consumption and a carbon dioxide production of the individual.

16. The measuring and fitting device according to claim 1, wherein a carbon dioxide partial pressure in the blood circulation is in the range of 1 kPa to 20 kPa.

17. The measuring and fitting device according to claim 1, wherein the first carbon dioxide detection means is arranged for detecting a parameter relating to a carbon dioxide partial pressure in the arterial blood stream.

18. The measuring and fitting device according to claim 1, wherein the computer is adapted to determine two or more parameters relating to an equilibrium state of an overall oxygen uptake or consumption and carbon dioxide elimination or production based on the output of at least one of the oxygen and one of the carbon dioxide detection means, to compare said parameter(s) with predefined threshold value(s) and to produce a control data item accordingly if said parameter(s) exceed said threshold value(s).

19. A method for determining at least three respiratory parameters in an individual comprising:
providing the measuring and fitting device of claim 1; and
determining the at least three respiratory parameters in the individual.

20. The method of claim 19, wherein said individual is a healthy individual.

21. The method of claim 19, wherein said individual is considered to have a risk of suffering from oxygen and carbon dioxide pulmonary gas exchange problems.

22. The method of claim 19, wherein said individual is suffering from oxygen and/or carbon dioxide pulmonary gas exchange problems.

23. A computer system comprising at least one general purpose computer having one or more computer programs stored within data storage means associated therewith, the computer system being arranged for as well as being adapted for determining the at least three respiratory parameters relating to the individual according to claim 1.

24. A computer program product embodied on a computer readable medium being adapted to enable a computer system according to claim 23 to determine at least three respiratory parameters of the individual.

25. The measuring and fitting device according to claim 1, wherein the computer controls the first control means controlling the flow of the first gas.

26. The measuring and fitting device according to claim 1, wherein the parameter indicative of ventilation of the individual is a ventilation distribution of the individual, the ventilation distribution representing a fraction of ventilation going to different ventilated compartments of a lung model, and
wherein the parameter indicative of perfusion of the individual is a perfusion distribution of the individual, the perfusion distribution representing a fraction of perfusion going to the different ventilated compartments of the lung model.

27. The measuring and fitting device according to claim 1, wherein the determination of said set of at least three respiratory parameters includes iteratively trying different sets of values for said set of at least three respiratory parameters and for each attempt, determining the consistency measure to evaluate how well the model prediction correlate with the measured data.

28. A method of automatically estimating respiratory parameters of an individual, the method comprising the steps of:
automatically measuring a level of oxygen in a blood circulation of the individual thereby producing a first output;
automatically measuring the level of oxygen in gas flow passing into or out of the respiratory system of the individual thereby producing a second output to the computer;
automatically measuring a level of carbon dioxide in the blood circulation of the individual thereby producing a third output;
automatically measuring the level of carbon dioxide in the gas flow passing into or out of the respiratory system of the individual thereby producing a fourth output;
automatically retrieving and storing at least two oxygen measurements and one carbon dioxide measurement, the oxygen measurements being a first concurrent output comprising the first output and the second output concurrently within a first data structure, in which the stored first output and the stored second output are mutually related and related to a stored oxygen measurement at a corresponding level of oxygen in the gas flow passing into the respiratory system, the carbon dioxide measurement being a second concurrent output comprising the third output and the fourth output concurrently produced within a second data structure, in which the stored third and fourth outputs are mutually related and related to a stored carbon dioxide measurement at a corresponding level of oxygen in the gas flow passing into the respiratory system;

automatically constructing a first output versus second output curve by fitting the at least two oxygen measurements;

automatically constructing a gas exchange fitting model based on the fitted curve in combination with the carbon dioxide measurement, the gas exchange fitting model being a three-parameter model, at least two of the three parameters being a parameter indicative of ventilation of the individual and a parameter indicative of perfusion of the individual;

automatically determining, based on the at least two oxygen measurements and one carbon dioxide measurement, a consistency measure indicative of quality of the fitting model;

automatically determining a number of additional measurements required to improve the gas exchange fitting model, the gas exchange fitting model stored in a computer for use; and automatically estimating the respiratory parameters of the individual using the gas exchange fitting model.

29. The method according to claim 28, wherein the gas exchange fitting model is based on a lung model, the lung model comprising two ventilated compartments and a pulmonary shunt compartment.

30. The method according to claim 29, wherein the three parameters includes a ventilation distribution between the ventilated compartments and a perfusion distribution between the ventilated compartments.

31. The method according to claim 28, further comprising the step of automatically assessing a timing of measurements.

32. The method according to claim 28, further comprising the steps of automatically assessing an appropriate level of the second output to achieve a target level of the first output and automatically controlling the level of the second output.

33. The method according to claim 28, further comprising the step of automatically monitoring steady states or equilibrium of the pulmonary gas exchange system of the individual.

* * * * *